（12） United States Patent
Kuan et al.

(10) Patent No.: US 9,689,854 B2
(45) Date of Patent: *Jun. 27, 2017

(54) FOOD SAFETY DETECTION DEVICE AND MANUFACTURING METHOD FOR THE SAME

(71) Applicant: National Tsing Hua University, Hsinchu (TW)

(72) Inventors: Chen-Meng Kuan, Hsinchu (TW); Roger L. York, Hsinchu (TW); Robert S. Langer, Hsinchu (TW); Chao-Min Cheng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 284 days.

This patent is subject to a terminal disclaimer.

(21) Appl. No.: 14/524,617

(22) Filed: Oct. 27, 2014

(65) Prior Publication Data

US 2015/0044761 A1 Feb. 12, 2015

Related U.S. Application Data

(63) Continuation-in-part of application No. 13/945,237, filed on Jul. 18, 2013, now Pat. No. 9,063,128.

(30) Foreign Application Priority Data

Jun. 25, 2013 (TW) .............................. 102122514 A

(51) Int. Cl.
*G01N 33/02* (2006.01)
*B05D 3/10* (2006.01)
*B05D 7/06* (2006.01)
*G01N 33/52* (2006.01)
*G01N 33/04* (2006.01)
*B05D 3/12* (2006.01)

(52) U.S. Cl.
CPC ............... *G01N 33/02* (2013.01); *B05D 3/12* (2013.01); *B05D 7/06* (2013.01); *G01N 33/04* (2013.01); *G01N 33/523* (2013.01); *G01N 33/528* (2013.01)

(58) Field of Classification Search
None
See application file for complete search history.

(56) References Cited

U.S. PATENT DOCUMENTS

| 3,552,928 | A | * | 1/1971 | Fetter | ..................... C12C 21/54 422/421 |
| 4,960,548 | A | * | 10/1990 | Ikeda | ....................... B27N 3/22 209/139.1 |
| 5,918,981 | A | * | 7/1999 | Ribi | ......................... G01K 1/16 116/217 |
| 8,044,257 | B2 | * | 10/2011 | Song | .................... G01N 33/558 604/361 |
| 2005/0112023 | A1 | * | 5/2005 | Liang | .................. G01N 33/558 422/400 |
| 2010/0159599 | A1 | | 6/2010 | Song et al. | |
| 2011/0200999 | A1 | * | 8/2011 | Soni | ....................... C12Q 1/689 435/6.11 |

FOREIGN PATENT DOCUMENTS

| CN | 102401828 A | 4/2012 |
| TW | 201317361 A | 5/2013 |

OTHER PUBLICATIONS

Maldas, D. et al. 1989. Influence of coupling agents and treatments on the mechanical properties of cellulose fiber-polystyrene composites. Journal of Applied Polymer Science 37: 751-775. specif. pp. 751, 753.*

* cited by examiner

*Primary Examiner* — Renee Claytor
*Assistant Examiner* — Sharon M Papciak
(74) *Attorney, Agent, or Firm* — Muncy, Geissler, Olds & Lowe, P.C.

(57) ABSTRACT

A food safety detection device includes a xylem fiber substrate, which is configured with a sampling portion and a reaction portion. The reaction portion includes at least one chemical reagent. The sampling portion absorbs a test sample. The test sample moves on the xylem fiber substrate to the reaction portion and reacts with the chemical reagent. A manufacturing method for the food safety detection device is also disclosed. The food safety detection device is advantageous for easy operation, safety and rapid analysis.

12 Claims, 13 Drawing Sheets

FOOD SAFETY DETECTION DEVICE AND MANUFACTURING METHOD FOR THE SAME

CROSS REFERENCE TO RELATED APPLICATIONS

This application is a Continuation-In-Part of U.S. application Ser. No. 13/945,237 filed on Jul. 18, 2013, which claims priority under 35 U.S.C. §119(a) on Patent Application No(s). 102122514 filed in Taiwan, Republic of China on Jun. 25, 2013, the entire contents of which are hereby incorporated by reference.

BACKGROUND OF THE INVENTION

Field of Invention

The present invention relates to a detection device and a manufacturing method for the same. More particularly, the present invention relates to a detection device used for detecting food safety and a manufacturing method for the same.

Related Art

The food safety, such as the remained toxic materials, process pollutants and the likes, is always a concerned issue, so that the Food safety detections have become more and more important. For example, many food companies or stores may add overdosed or improper additives (e.g. color fasting agents, preservatives or the likes) in their food products. In another case, the final food products may still contain the undesired chemical substances such as pesticide reagent. For example, nitrite is usually added to food as a color fasting agent. If people eat the food product containing nitrite, it will cause the secondary amine reaction so as to generate the high hazard carcinogen—N-nitroso compounds.

In brief, to intake exceeded certain food additives can highly threaten the health of human bodies. Although the acceptable amounts of additives in food products have been listed by FDA to keep people away from the overdosed additives, it is still existing the unintentional mistakes on food treatments and it still cannot stop the unscrupulous companies. Therefore, it is desired to effectively detect the food additives before tasting food products.

There are many detection methods for detecting the food additives such as spectrophotometry, HPLC (high performance liquid chromatography), GC (gas chromatography), IC (ion chromatography), CE (capillaryelectrophoresis), polarography and FIA (flow injection analysis). However, these detection methods all need a high-tech and expensive equipment for detection, and require operators and a lot of time to precisely detect the additives in the labs.

As the rising of health and food safety consciousness, the concept of self-detection in house is more and more popular. The self-detection allows the users to easily and simply detect the food products anytime and anywhere. In general, this simple detection utilizes the color change of detection reagent to indicate the detection result, so the user can easily realize the detection result without additional equipment or with only a simple device. Moreover, when the color change reaches a dangerous range, the user can contact any related institute for further detailed detection. Accordingly, the self-detection has the advantages of convenience and low cost. The commonly used self-detection for detecting food additives mainly utilizes a testing strip containing a detection reagent to detect the food additives according to colorimetric method or photometric method. The user can compare the color of the testing strip with a given color table so as to determine the nitrite concentration in the food product. This simple measuring method brings the users an extremely large convenience and safety. However, the user has to carry the testing strip all the time, which may bother the users indeed. In addition, the existing testing strips are almost made by many processes, and the added substances in the testing strips will cause the risk of the safety of the testing strips.

Therefore, it is an important subject to provide a food safety detection device, which has the simple operation property as the existing testing strips, is capable of being applied to daily necessities and adopts special and natural material for improving the sampling and detecting speeds and the application safety, and a manufacturing method thereof.

SUMMARY OF THE INVENTION

In view of the foregoing subject, an objective of the present invention is to provide a food safety detection device, which has the simple operation property as the existing testing strips, is capable of being applied to daily necessities and adopts special and natural material for improving the sampling and detecting speeds and the application safety, and a manufacturing method thereof.

To achieve the above objective, the present invention discloses a food safety detection device including a xylem fiber substrate, which is configured with a sampling portion and a reaction portion. The reaction portion includes at least one chemical reagent. The sampling portion absorbs a test sample. The test sample moves on the xylem fiber substrate to the reaction portion and reacts with the chemical reagent.

In one embodiment, the xylem fiber substrate comprises cellulose, lignin and/or hemicellulose.

In one embodiment, the chemical reagent comprises a food additive reagent, a pesticide reagent, or a pathogenic microorganism reagent.

In one embodiment, the detection device is a stirring rod, a toothpick or a chopstick.

In one embodiment, the xylem fiber substrate is further configured with a transmission portion connected to the sampling portion and the reaction portion, and at least a part of the transmission portion is processed by hydrophobic surface treatment.

In one embodiment, the reaction portion has an accommodating space and a bulk body. The accommodating space is formed on a surface of the xylem fiber substrate. At least a part of the bulk body is disposed in the accommodating space, and the chemical reagent is disposed on the bulk body.

In one embodiment, the accommodating space is disposed between an opened part and a main part of the xylem fiber substrate, and the opened part is at least partially connected to the main part.

In one embodiment, the proportion of α-cellulose in the bulk body is greater than that in the reaction portion.

In one embodiment, the densification property of the bulk body is greater than that of the reaction portion.

To achieve the above objective, the present invention also discloses a manufacturing method for a food safety detection device. The manufacturing method includes the steps of: providing a xylem fiber substrate; forming a sampling portion and a reaction portion on the xylem fiber substrate; and disposing at least a chemical reagent in the reaction portion so as to form the detection device.

In one embodiment, the step of providing the xylem fiber substrate includes to provide a raw material containing xylem fiber and to physically process the raw material to extract the xylem fiber substrate.

In one embodiment, the xylem fiber substrate comprises cellulose, lignin and/or hemicellulose.

In one embodiment, the chemical reagent comprises a food additive reagent, a pesticide reagent, or a pathogenic microorganism reagent.

In one embodiment, the detection device is a stirring rod, a toothpick or a chopstick.

In one embodiment, before the step of providing the xylem fiber substrate, the manufacturing method further includes a step of shaping the xylem fiber substrate to a shape of stirring rod, a toothpick or a chopstick.

In one embodiment, the manufacturing method further includes the steps of: disposing a transmission portion on the xylem fiber substrate, wherein the transmission portion connects to the sampling portion and the reaction portion; and processing at least a part of the transmission portion by hydrophobic surface treatment.

In one embodiment, the manufacturing method further includes the steps of: forming an accommodating space and a bulk body in the reaction portion, wherein the accommodating space is formed on a surface of the xylem fiber substrate, and at least a part of the bulk body is disposed in the accommodating space; and disposing the chemical reagent on the bulk body.

In one embodiment, the accommodating space is disposed between an opened part and a main part of the xylem fiber substrate, and the opened part is at least partially connected to the main part.

In one embodiment, the proportion of $\alpha$-cellulose in the bulk body is greater than that in the reaction portion.

In one embodiment, the densification property of the bulk body is greater than that of the reaction portion.

As mentioned above, the food safety detection device of the present invention has a reaction portion containing the chemical reagent for effectively detecting a specific test target such as the concerned nitrite or nitrate in food safety. The food safety detection device includes a main structure composed of xylem fiber substrate, which has excellent absorptive property for water molecules, so that the detection speed can be improved due to the enhanced capillary phenomenon of the liquid test sample in the detection device. In addition, the conventional testing strips, which are made by multiple processes, may contain some residual prohibited or harmful chemical reagents used in the processes, so the food products cannot be served after being detected by the conventional testing strips. In contrary, the food safety detection device of the invention is made of the natural xylem fiber substrate, so it can directly contact or be inserted into a sample and the tested sample can be still served after the detection. Besides, the present invention also has the advantages of lower cost and easy production. Preferably, the xylem fiber substrate has a strengthened mechanical structure and better pH durability than the conventional testing strips (made by papers).

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1A:
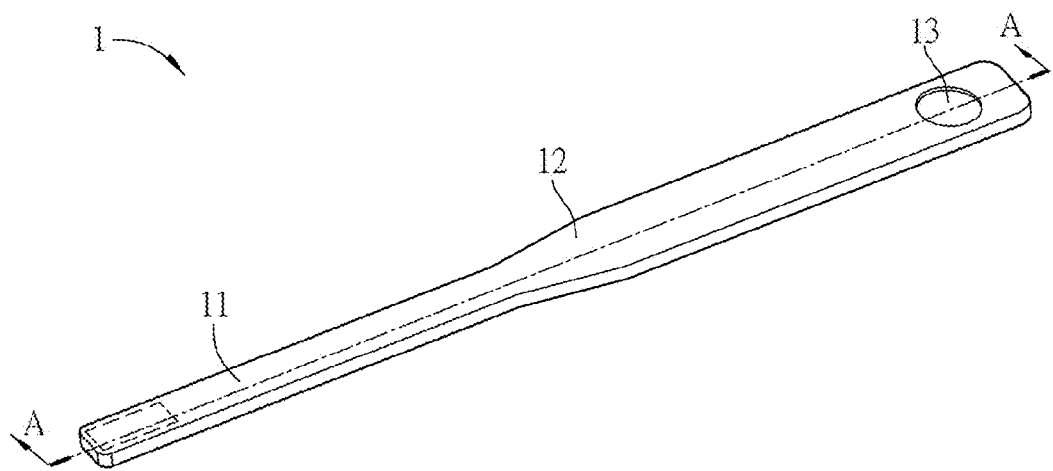
FIG. 1A is a schematic diagram of a detection device according to a preferred embodiment of the invention.
Figure 1B:
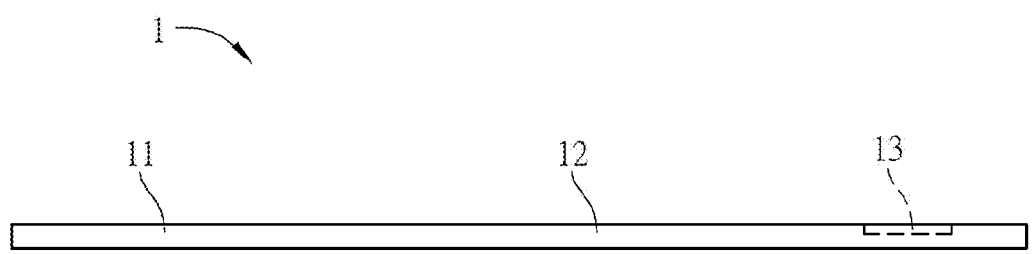
FIG. 1B is a sectional view along the line A-A of FIG. 1A.

FIG. 1A is a schematic diagram of a food safety detection device 1 (referring to detection device 1 hereinafter) according to a preferred embodiment of the invention, and FIG. 1B is a sectional view along the line A-A of FIG. 1A. Referring to FIGS. 1A and 1B, the detection device 1 of the embodiment is used to sample and detect a test sample, such as a biological fluid or food product. Although this embodiment does not limit the type of the test sample, the following descriptions will focus on the food safety related samples such as the soup of hot pot or the biological fluid (e.g. saliva) of a food poisoning patient for rapidly diagnosing the pathogeny.

In order to be properly applied to the daily necessities, the detection device 1 can be functioned as a stirring rod, a chopstick, a toothpick or the likes, which also has the additional detection function. In other words, the above examples are essential products for many users, which means that the users do not carry any additional necessity along with themselves for the detection purpose. In this embodiment, the detection device 1 is a stirring rod as an example.

Figure 2:
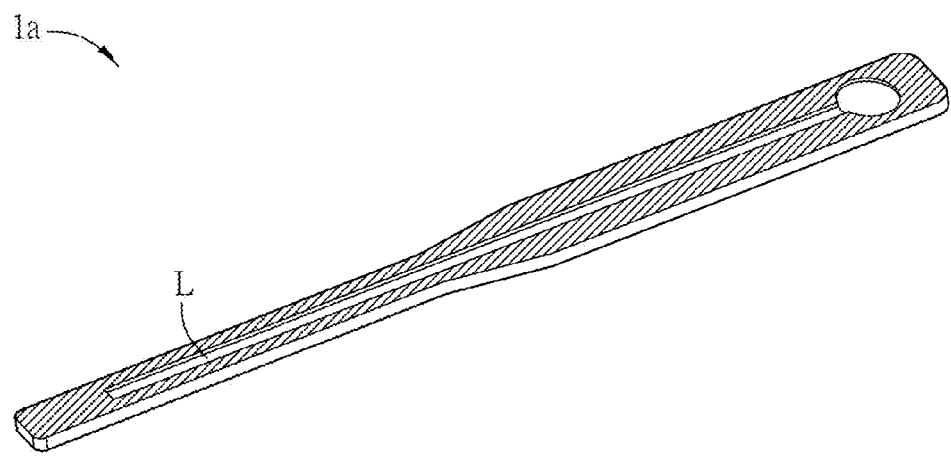
FIG. 2 is a schematic diagram of a detection device according to another preferred embodiment of the invention.

Referring to FIGS. 1A and 1B, the detection device 1 of the embodiment has a xylem fiber substrate. In other words, the detection device 1 is a structure at least partially made by the xylem fiber substrate. In the practice manufacturing procedure, the detection device 1 is preferably made by the xylem fiber substrate entirely. Of course, the concept of this invention also includes the case that the detection device has only a part to be made by the xylem fiber substrate for transmitting the test sample (a "flowing channel"). As shown in FIG. 2, the detection device 1a has a channel structure L extending along the axial direction thereof. The channel structure L is entirely made by the xylem fiber substrate, and the residual part of the detection device 1a other than the channel structure L may include any suitable material other than the xylem fiber substrate. The material of the residual part has a hydrophilic property poorer than the xylem fiber substrate, and this invention is not limited.

Regarding to the major functional compositions, the xylem fiber substrate of the detection device 1 is configured with a sampling portion 11, a transmission portion 12 and a reaction portion 13. The sampling portion 11, the transmission portion 12 and the reaction portion 13 are adjacently disposed in sequence. In practice, the shape and size of each portion are not limited, and they can be designed based on the test sample or the detection target. The actual shape of each portion can be, for example but not limited to, cylinder, rectangular or plate, and this invention is not limited.

Herein, the term "xylem fiber substrate" means the woody fibrous tissue of a plant. In this invention, the xylem fiber substrate includes cellulose, hemicellulose, pectin and/or lignin, which has better absorption property for water molecules. Accordingly, the test sample can be transmitted from the sampling portion 11 to the reaction portion 13 through the transmission portion 12 (via the pores in the xylem fiber substrate).

The raw material of the detection device 1 can be a wood or bamboo piece, and preferably selected from any woody plant with high-degree woody tissues such as shrubs or arbors. In practice, the stirring rod, chopstick or toothpick made by the woody tissue can be further processed to obtain the detection device 1. Since the conventional testing strips may contain some residual prohibited or harmful chemical reagents used in the manufacturing processes, so the food products cannot be served after being detected by the conventional testing strips. In contrary, the detection device 1 of the embodiment is made of a xylem fiber substrate, which is a natural material and has higher safety. During the detection, the detection device 1 can be directly applied to or inserted into a sample and the tested sample can be still served after the detection without any additional treatment (e.g. the treatment for removing remained chemical reagent or harmful substances). Besides, the xylem fiber substrate is a natural material, so it has the advantages of lower cost and easy processing.

In addition, the xylem fiber substrate has a strengthened mechanical structure and better pH durability than the conventional testing strips (made by papers).

With reference to FIGS. 1A and 1B, the test sample is transmitted to the reaction portion 13 through the transmission portion 12. In order to remove the impurity in the test sample for enhancing the detection accuracy, the sampling portion 11 can be configured with a filter layer (as the dotted line area of FIG. 1A). The shape, size and location of the filter layer can be designed according to the actual need and is not limited in this embodiment. For example, when the amount of the test samples is quite large, a large sized filter layer can be selected for improving the filtering effect.

Figure 3:
FIG. 3 is a sectional view of a detection device according to another preferred embodiment of the invention.

In this embodiment, the reaction portion 13 is a recess. The shape and size of the recess can be designed according to the actual need and is not limited in this embodiment. The recess shown in FIGS. 1A and 1B is for an illustration only and is not to limit the scope of the invention. In practice, the shape of the reaction portion 13 can be, for example but not limited to, rectangular, square, cylinder, hemisphere, V-shape, or any other suitable shapes. As shown in FIG. 3, the reaction portion 13b of the detection device 1b is V-shaped. This structure is helpful to observe the color result on the side wall 131b, thereby improving the accuracy of the detection. To be noted, the location of the reaction portion is flexible depending on the detection requirement, and this invention is not limited.

In order to achieve the detection purpose, a plurality of chemical reagents is configured in the reaction portion 13. Since the detection device 1 is applied to food safety detection, the detection targets of the detection device 1 may include, for example, the food raw materials or the residual substances from the manufacturing processes, such as the food additive reagent, pesticide reagent, or pathogenic microorganism reagent. For example, nitrite is a commonly used color fasting agent. The nitrite added in meat may react with the amino acid during cooking or in mouth and thus generate the high hazard carcinogen—N-nitroso compound, so it is a very common detection target. Accordingly, the detection device 1 of this embodiment is applied to detect nitrite group, and the following analysis and determination.

Herein, the chemical reagents are firmly or unfirmly disposed in the reaction portion 13. The means for firmly disposing the chemical reagent in the reaction portion 13 includes to connect a specific functional group of the chemical reagent to the reaction portion 13 by, for example but not limited to, covalent bonds. The means for unfirmly disposing the chemical reagent in the reaction portion 13 includes to dispose the chemical reagent in the reaction portion 13 by coating or the likes.

As shown in FIG. 1B, the chemical reagent is disposed on the bottom of the reaction portion 13, but this invention is not limited thereto. In other embodiments, the chemical reagent can be disposed at the side surface of the reaction portion 13 only or be disposed at the side surface and bottom of the reaction portion 13 both.

In addition, it is also possible to dip the reaction portion 13 into the chemical reagent solution for attaching to the detection reagent in the reaction portion 13. In more specific, the chemical reagent can be attached to the reaction portion 13 due to the capillary action of the xylem fiber substrate and the vascular tissue of the plant fiber.

Furthermore, when the detection device 1 is applied to detect nitrite groups, the chemical reagent can be selected from the composition containing sulfanilamide, citrate acid and N-(1-naphthyl)ethylenediamine or the composition containing Sulfanilic acid, 1-naphthylamine and acetic acid. If the test sample contains nitrite ions (nitrite), it will react with the chemical reagent so that the detection device 1 shows a specific color followed by a proper qualitative test. The method for disposing the chemical reagent in the reaction portion 13 is well known to the skilled person, so the detailed description and the similar methods will be omitted hereinafter.

To be noted, this invention is not limited to the above examples, and for example, the detection device 1 can also be applied to detect other food additives such as bleaches, water retention agents or preservatives. In more detailed, the food bleaches may include hydrogen peroxide ($H_2O_2$) and sodium sulfite. Although hydrogen peroxide is allowed to be used in food product processes (excluding wheat powder and its related products) for the purpose of sterilization and bleaching, the final food products are not allowed to contain any residual hydrogen peroxide. This is because the boiling point of hydrogen peroxide is too high (152° C.), so the residual hydrogen peroxide cannot be removed by boiling water. If the user eats the food products containing hydrogen peroxide all the time, it may be harmful to the health thereof. Similarly, although the water retention agent (e.g. phosphate) is allowed to be used in the food processes (under the maximum limit dose), it still cannot be added to fresh meat. If people intake exceeded amount of phosphate, it will cause the unbalance between calcium and phosphor in human body. This unbalance may cause hyperphosphatemia or hypocalcemia and thus result in the calcification of Non-skeletal tissues such as the calcification of kidney which can affect the renal function. In addition, the preservatives such as borax or benzoic acid can be used in food products to prevent food poison caused by microorganism. Unfortunately, if the added preservatives are overdosed or improperly added, it is highly risk to cause poison or cancer to human bodies. Therefore, the detection device 1 of this embodiment can play a critical role for detecting and guarding the above food additives. The specific aspects can be varied according to the source of the detected target such as the food raw materials or soup. The reaction portion 13 can be configured with a proper detection reagent corresponding to these potential test samples for executing the desired detection. Similarly, the location and amount of the detection reagent can be designed depending on the actual requirement, and this invention is not limited.

In addition, the detection device 1 can be further used to detect the remained pesticide reagent in food products, such as pyrethroid insecticides or herbicides. The synthesized pyrethroid insecticides include cypermethrin, cyfluthrin, lambda-cyhalothrin, deltamethrin, cyphenothrin, fenvalerate and fluvalinate, and the herbicides include paraquat. Regarding to the above pesticide reagent, the detection device 1 of this embodiment can provide a rapid and clear detection result, so that the medical staffs can do the proper action to the patient as soon as possible. In more detailed, when a patient has taken pesticide reagent, the medical staffs can use the detection device 1 to check the status before the therapy or to follow the treatment status during the therapy.

In addition, the detection device 1 can be further applied to detect microorganisms in the food safety field. Taking the milk as an example, the pollution in the procedures of collecting milk from cows, packing and sterilization, the bacterial contamination can occur at any of the above procedures. The bacteria can not only turn sour the milk but also cause some diseases, which all threaten the health of human body. The detection device 1 can be used to detect the food product by detecting, for example, the remained compounds, chemicals, additives and/or microorganisms in the food product. In more specific, the detection device 1 can detect the pH value of the milk (sour level) and/or microorganisms in the milk. To be noted, the detection method for remained compounds, chemicals or microorganisms is the same as the above detection methods and the experimental examples will be discussed hereinafter, so the detailed description thereof will be omitted here.

After configuring the detection device 1, it can be used to detect food products later. In practice, the user can bring the detection device 1 (the sampling portion 11) to contact the test sample or drop the test sample on the sampling portion 11, then the test sample will be transmitted from the sampling portion 11 to the reaction portion 13 through the transmission portion 12 by capillary action. If the test sample contains nitrite, it will react with the chemical reagent in the reaction portion 13 to generate purple red azo compound. Accordingly, the detection device 1 can detect whether the test sample contains nitrite or not, thereby improving the personal safety. Of course, if it is desired to determine whether the contained amount of nitrite in the test sample is over the safety limitation, the detection device 1 can also provide a quantification function by colorimetric method. Preferably, the detection device 1 of the invention is designed in the form of daily necessities so as to increase the convenience.

Figure 4A:
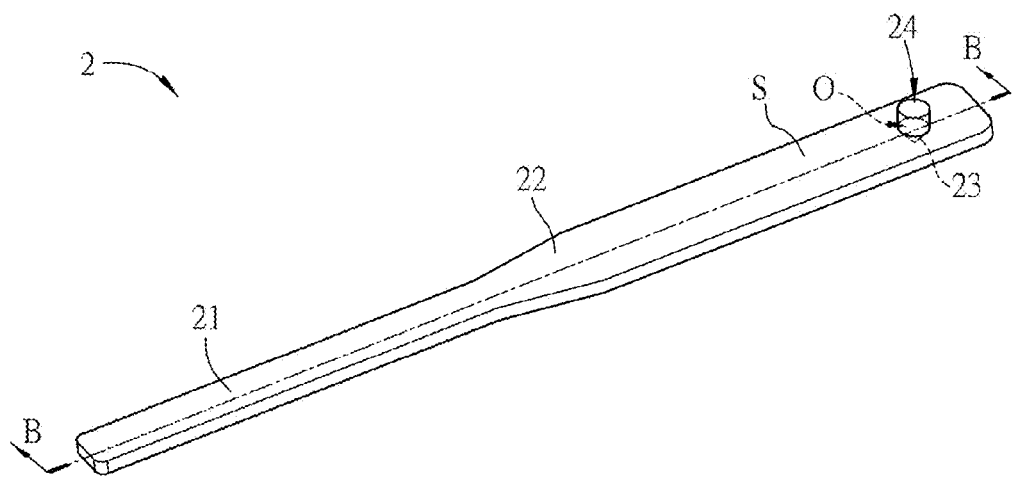
FIG. 4A is a schematic diagram of a detection device according to another preferred embodiment of the invention.
Figure 4B:
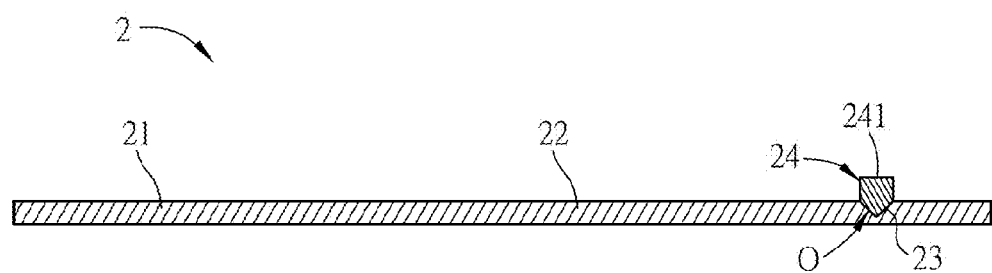
FIG. 4B is a sectional view along the line B-B of FIG. 4A.

The above mentioned aspect of the detection device 1 is not to limit the scope of the invention. FIG. 4A is a schematic diagram of a detection device 2 according to another preferred embodiment of the invention, and FIG. 4B is a sectional view along the line B-B of FIG. 4A. With reference to FIGS. 4A and 4B, the detection device 2 is mostly the same as the previous detection device 1b, but the reaction portion 23 of the detection device 2 includes an accommodating space O and a bulk body 24. The accommodating space O is formed on a surface S of the xylem fiber substrate. In this embodiment, at least a part of the bulk body 24 is disposed in the accommodating space O, and it is perpendicular to the long axis direction of the detection device 2. Accordingly, the bulk body 24 can provide an extended flow channel for the test sample. In practice, the chemical reagent can be disposed at one surface 241 of the bulk body 24, and the test sample is transmitted from the sampling portion 21 to the reaction portion 23 and the bulk body 24 through the transmission portion 22 by capillary action.

To be noted, since the detection device 2 has additional bulk body 24 perpendicular to the reaction portion 23, it can act as a three-dimensional detection device in view of the flowing direction of the test sample.

The xylem fiber substrate of this embodiment is a bamboo material, and the material of the bulk body 24 is a woody material such as birch, aspen or pine materials. Preferably, the densification property of the bulk body (woody material) is greater than that of the reaction portion (bamboo material). The term "densification property" represents the densification of the components (e.g. fiber) in the woody and bamboo materials. When the test sample flows from the reaction portion 23 to the bulk body 24 by capillary action, the flow speed thereof will be slowed down due to the different densification properties. Accordingly, the flow speed can be controlled in the detection, and the test sample can have enough time the finish the desired reaction with the chemical reagent, thereby improving the detection effect of the detection device 2. Of course, the densification properties of the bulk body 24 and the reaction portion 23 are not limited in this invention, and the user can design the desired configurations depending on the actual requirement.

In practice, the material of the bulk body 24 can be the purified α-cellulose. When the proportion of α-cellulose in the bulk body 24 is greater than that in the xylem fiber substrate (preferably the reaction portion 23), the hydrophilic property of the bulk body 24 is better than that of the reaction portion 23. Accordingly, when the test sample flows from the reaction portion 23 to the bulk body 24 by capillary action, the flow speed thereof will increase due to the difference of the hydrophilic properties. In other words, the above design of the bulk body 24 can increase the reaction time of the test sample and speed up the total reaction so as to reduce the detection time. Besides, the needed sample amount can be reduced in this embodiment.

In addition, the shape of the bulk body 24 is, for example but not limited to, cylinder. In practice, the shape of the bulk body 24 can also be a plate shape, and it depends on the structure of the reaction portion 23.

Figure 5A:
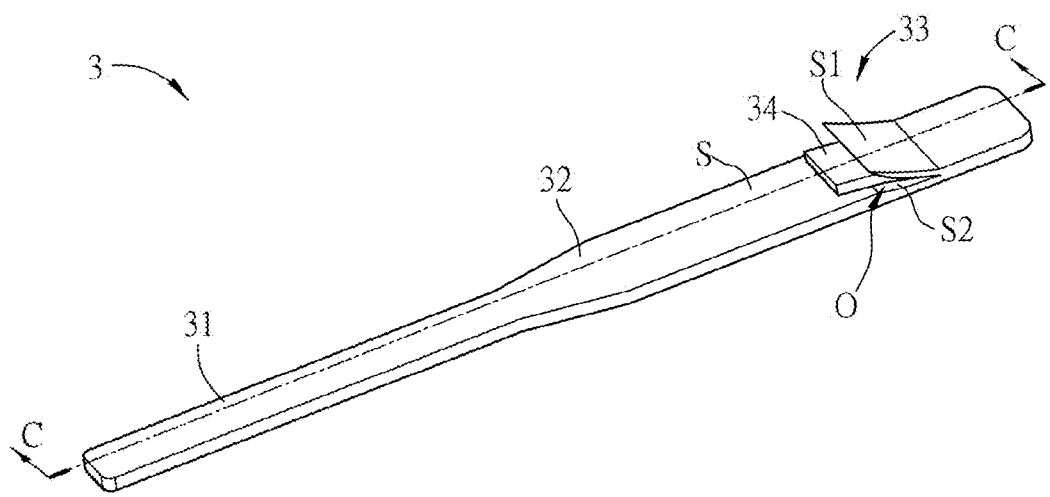
FIG. 5A is a schematic diagram of a detection device according to another preferred embodiment of the invention.
Figure 5B:
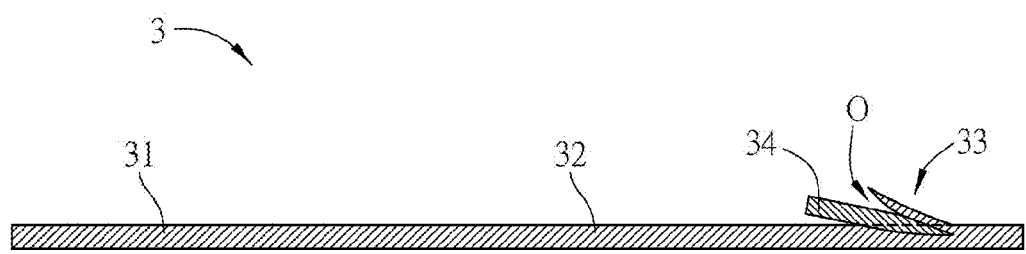
FIG. 5B is a sectional view along the line C-C of FIG. 5A.

In another embodiment, the reaction portion can also be extended by the configurations as shown in FIGS. 5A and 5B. In this embodiment, the detection device 3 comprises a sampling portion 31, a transmission portion 32 and a reaction portion 33, and is mostly the same as the previous detection device 1, but the reaction portion 33 includes an accommodating space O, which is formed by, for example, cutting a part of the detection device 3. Herein, the accommodating space O is disposed between an opened part S1 and a main part S2 of the xylem fiber substrate, and the opened part S1 is at least partially connected to the main part S2. Accordingly, the accommodating space O has a V-shaped structure. When the bulk body 34 is disposed in the accommodating space O, the detection device 3 can also provide an extended flow channel for the test sample. The materials and implements of the bulk body 34 are mostly the same as those of the above embodiment, so the detailed description thereof will be omitted.

To be noted, the method for disposing the bulk body 24, 34 in the reaction portion 23, 33 is not limited, and any approach capable of contacting the bulk body 24, 34 with the reaction portion 23, 33 is applicable. Besides, the bulk body 24, 34 can be disposed in the reaction portion 23, 33 by embedding, wedging or adhering.

Furthermore, when the bulk body 24, 34 is detachable from the reaction portion 23, 33, the bulk body 24, 34 can be taken out of the reaction portion 23, 33 after the reaction for performing any other analysis.

Figure 6A:
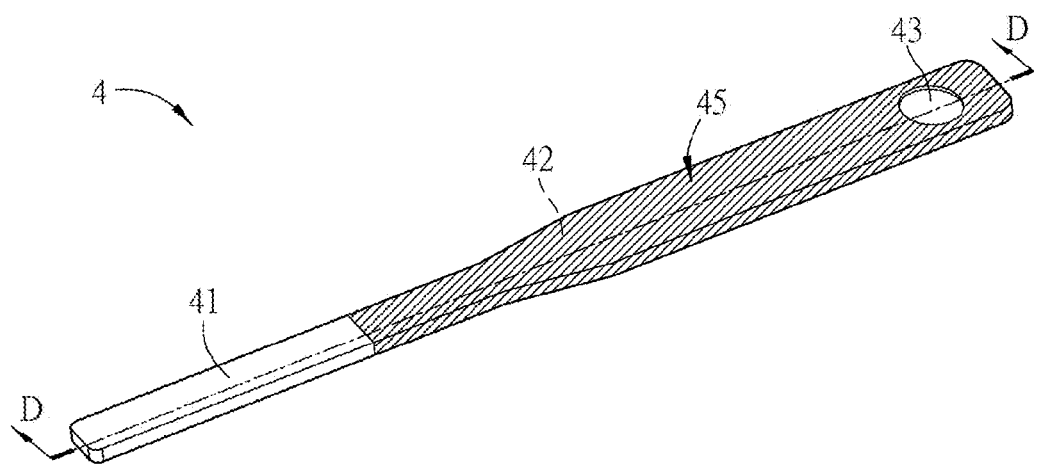
FIG. 6A is a schematic diagram of a detection device according to another preferred embodiment of the invention.
Figure 6B:
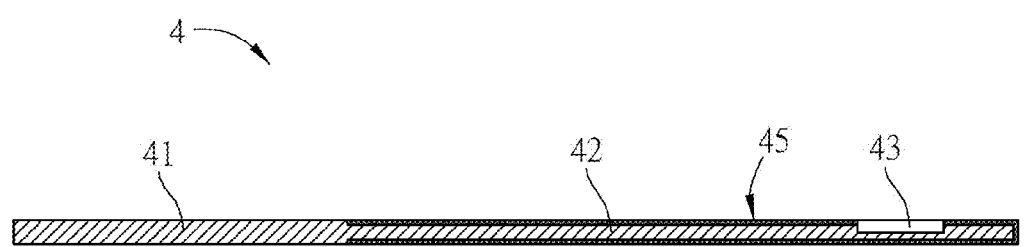
FIG. 6B is a sectional view along the line C-C of FIG. 6A.

FIG. 6A is a schematic diagram of a detection device 4 according to another preferred embodiment of the invention, and FIG. 6B is a sectional view along the line C-C of FIG. 6A. With reference to FIGS. 6A and 6B, the detection device 4 comprises a sampling portion 41, a transmission portion 42 and a reaction portion 43, and is mostly the same as the previous detection device 1, but the transmission portion 42 and the reaction portion 43 of the detection device 4 are processed by additional surface treatment (the dark region 45 of FIGS. 6A and 6B) so as to increase the stability of the xylem fiber. Herein, the surface treatment is, for example but not limited to, a hydrophobic treatment. The used hydrophobic reagent includes, for example but not limited to, PDMS (polydimethylsiloxane), which is coated on at least part surfaces of the transmission portion 42 and the reaction portion 43. The above additional surface treatment can define and minimize the hydrophilic areas contained in the transmission portion 42 and the reaction portion 43, so that the test sample can be precisely transmitted to the reaction portion 43 via the hydrophilic areas and then properly react with the chemical reagent.

The hydrophobic treatment is not limited. In practice, it is also possible to coat a photoresist layer on the hydrophilic detection device 4 to achieve the desired treatment. In more specific, when a SU-8 epoxy-based negative photoresist is coated on the detection device 4, the areas irradiated by UV light will not be dissolved in the developing solution so as to form the hydrophobic areas while the areas that is not irradiated by UV light can be exposed and express the original hydrophilic property. To be noted, the above methods and any similar method are well known to the skilled person in the art, so the detailed description thereof will be omitted.

Figure 7:
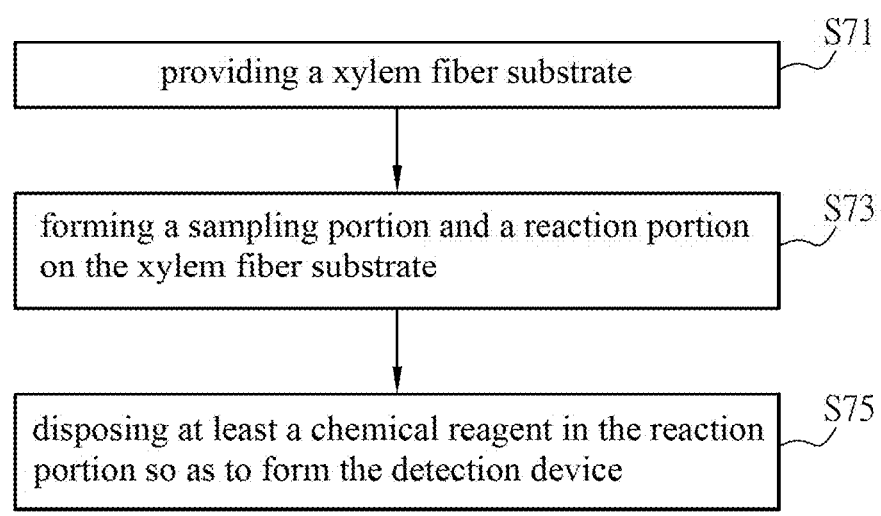
FIG. 7 is a flow chart of a manufacturing method for a detection device according to a preferred embodiment of the invention.

FIG. 7 is a flow chart of a manufacturing method for a detection device according to a preferred embodiment of the invention. Referring to FIG. 7, the manufacturing method for a detection device of the embodiment includes the following steps of: providing a xylem fiber substrate (S71); forming a sampling portion and a reaction portion on the xylem fiber substrate (S73); and disposing at least a chemical reagent in the reaction portion so as to form the detection device (S75). The step S71 of providing the xylem fiber substrate includes to provide a raw material containing xylem fiber and to physically process the raw material to extract the xylem fiber substrate. Any applicable physically process is acceptable, and this invention is not limited. In addition, the method for forming the sampling portion and the reaction portion is, for example but not limited to, slightly processing the xylem fiber substrate by physical method so as to define the location of each portion. Different manufacturing methods can be provided for various aspects of detection devices. For example, when the detection device is a toothpick, one end of the detection device is cut into a sharp tip for providing the function of toothpick. To be noted, the above mentioned aspects of detection devices can all be manufactured based on the principle of the disclosed manufacturing method of the embodiment with any proper modification according to the actual structure and requirement. The steps of the manufacturing method for the detection device and the components thereof have been discussed in the above embodiments, so the detailed descriptions thereof will be omitted here.

The actual operation and effect of the detection device 1 will be discussed in the following experimental examples. To be noted, the following examples are for illustrations only so that the skilled person can realize and repeat this invention. Of course, the detection devices of other embodiments can also be used to achieve the same goal, and this invention is not limited.

Experimental Example 1: Detecting Nitrite by the Detection Device 1

The chemical reagent is dropped (by micropipette (Gilson, Inc.)) onto the reaction portion 13 of the detection device 1. The chemical reagent includes 50 mmol/L sulfanilamide (≥99%, Sigma-Aldrich), 330 mmol/L citric acid (≥99.5%, Sigma-Aldrich) and 10 mmol/L N-(1-naphthyl) ethylenediamine (≥98%, Sigma-Aldrich). After adding the chemical reagent, the detection device 1 is dried for 15 minutes at 25° C. Then, the sampling portion 11 of the detection device 1 is used to contact the test sample. The test samples include a buffer sample containing nitrite standard diluted in distilled deionized water and a food sample containing nitrite standard diluted in hot pot soup (spiking test). Waiting for 7 minutes, intensity of color shown in the reaction portion 13 is determined by ImageJ analysis software.

Figure 8A:
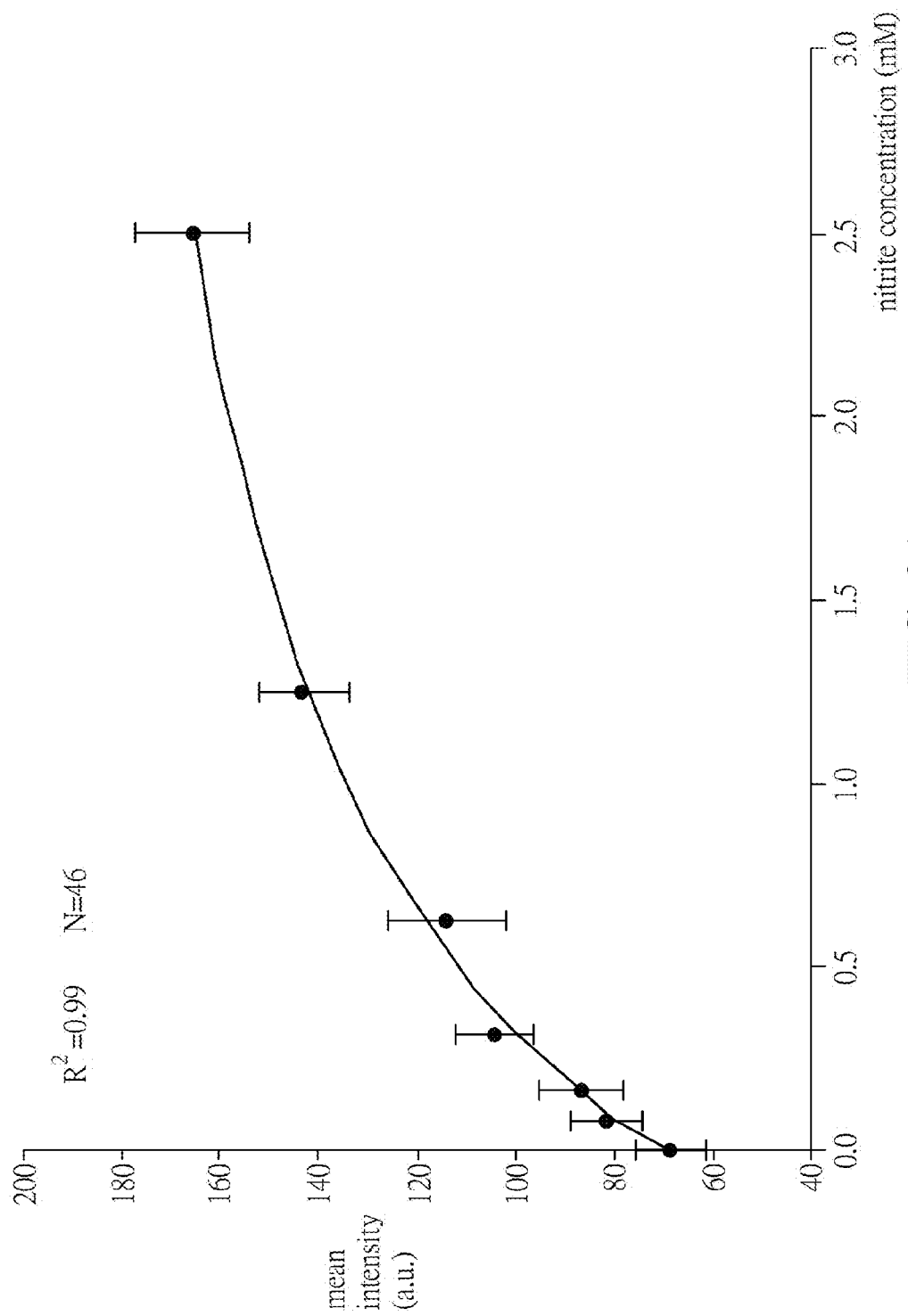
FIGS. 8A to 8C are schematic charts showing the detection results as using the detection device of FIG. 1 to detect nitrite.
Figure 8B:
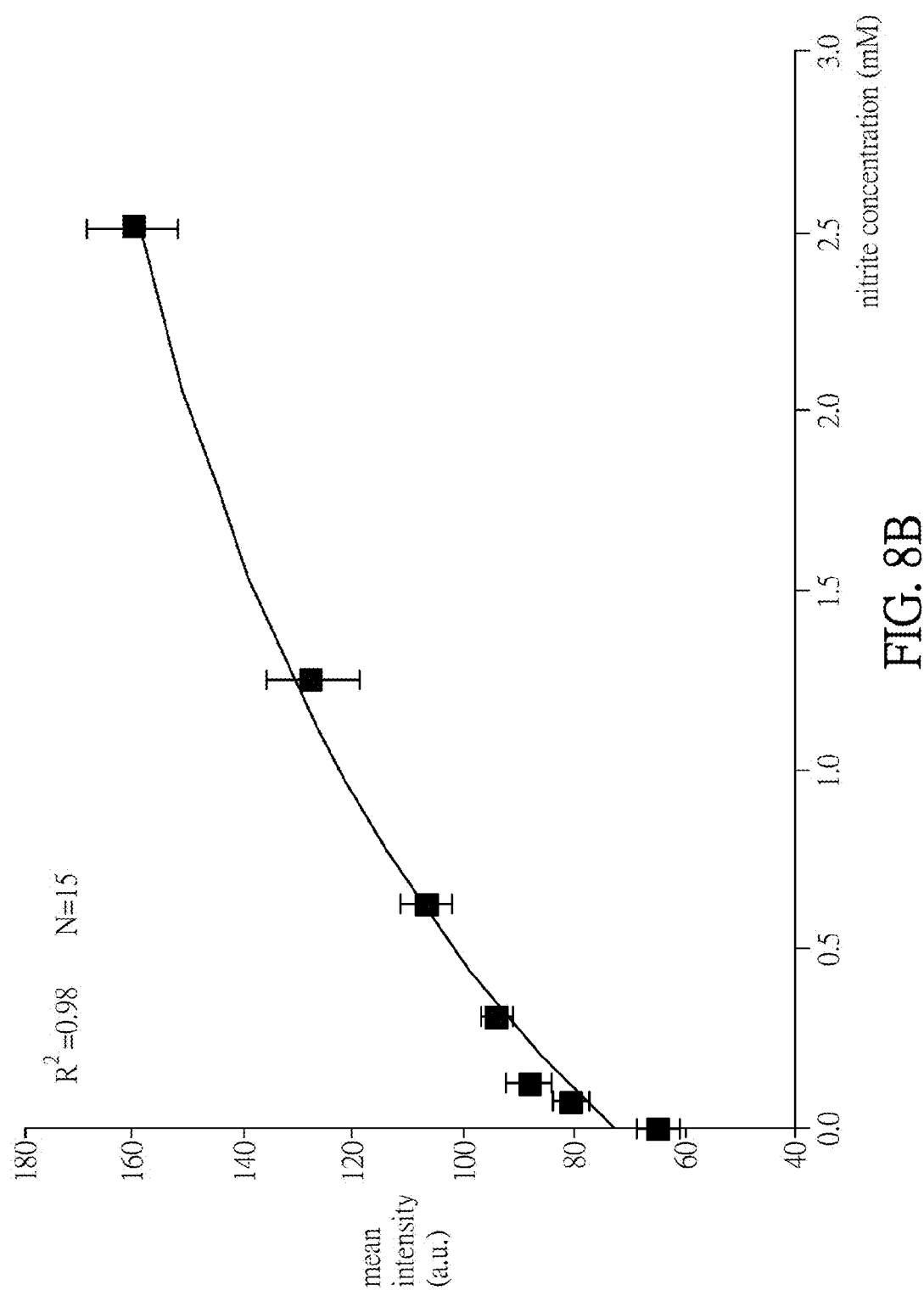
Figure 8C:
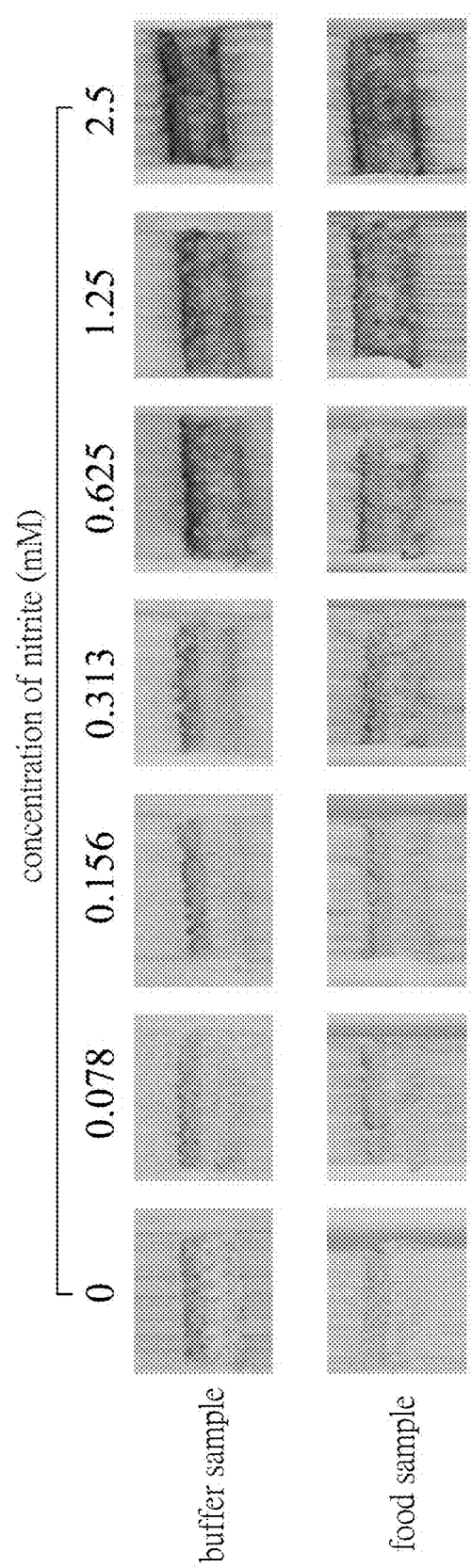

The analysis result is shown in FIGS. 8A and 8B. After the test sample reacts with the chemical reagent, the test result indicates that the detected mean intensity (which is represented in an arbitration unit, a.u.) of the color reaction increases as the nitrite concentration increases. As shown in FIG. 8C, comparing the tests of various nitrite concentrations in distilled deionized water (buffer sample) or in hot pot soup (food sample), the detected mean intensity of the color reaction also increases as the nitrite concentration increases.

Experimental Example 2: Detecting Nitrite by the Detection Device 2

The chemical reagent is dropped (by micropipette (Gilson, Inc.)) onto the extended reaction portion 24 of the detection device 2. The chemical reagent includes 50 mmol/L sulfanilamide (≥99%, Sigma-Aldrich), 330 mmol/L citric acid (≥99.5%, Sigma-Aldrich) and 10 mmol/L N-(1-naphthyl)ethylenediamine (≥98%, Sigma-Aldrich). After adding the chemical reagent, the detection device 1 is dried for 15 minutes at 25° C. Then, the sampling portion 21 of the detection device 2 is used to contact the test sample. The test samples are prepared by adding nitrite standards of different concentrations (0 mM, 0.156 mM, 0.625 mM and 1.25 mM) in distilled deionized water. Waiting for 7 minutes, intensity of color shown in the reaction portion 13 is determined by ImageJ analysis software.

Figure 9:
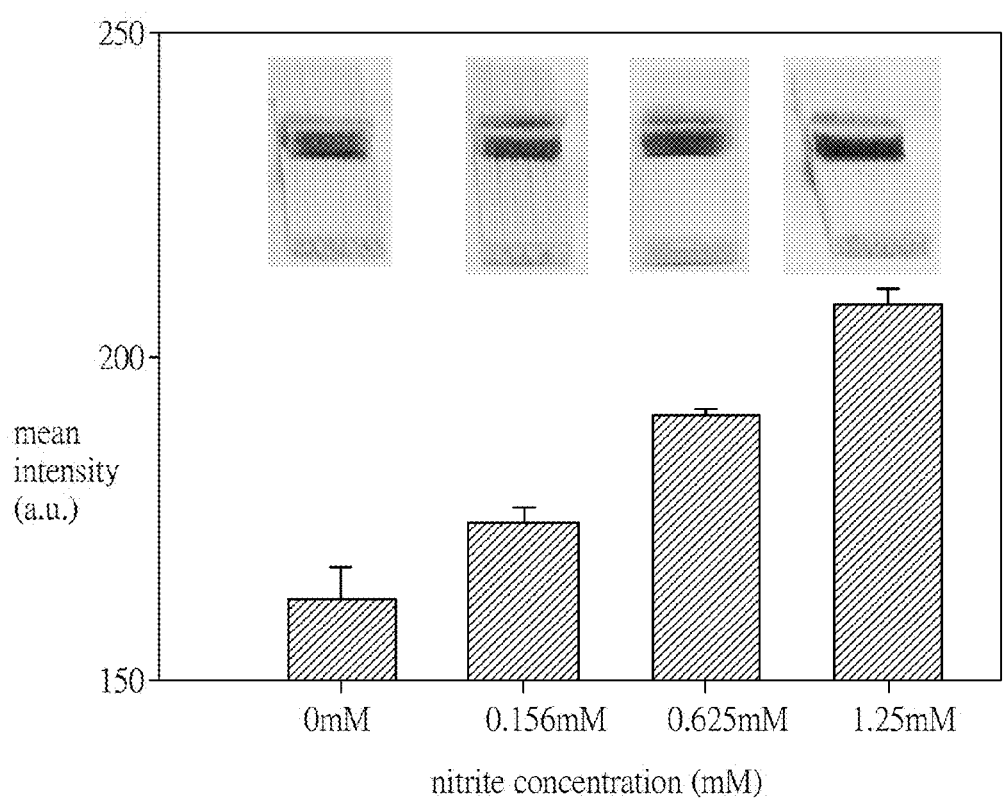
FIG. 9 is a schematic chart showing the detection result as using the detection device of FIG. 5A to detect nitrite.

The analysis result is shown in FIG. 9. After the test sample reacts with the chemical reagent, the test result indicates that the detected mean intensity (which is represented in an arbitration unit, au.) of the color reaction increases as the nitrite concentration increases. At the same time, the color of the reaction portion becomes darker as the nitrite concentration increases.

Experimental Example 3: Detecting Hydrogen Peroxide by the Detection Device 1

The chemical reagent (4 μL, 0.6M potassium iodide) is dropped (by micropipette (Gilson, Inc.)) onto the reaction portion 13 of the detection device 1. After adding the chemical reagent, the detection device 1 is dried for 10 minutes at 25° C. Then, the sampling portions 11 of the detection devices 1 (5 sets) are dipped into 0%, 0.3%, 0.5%, 1% and 15% hydrogen peroxide solutions, respectively, for 50 seconds, followed by the detection of the mean intensities of the 5 sets.

Figure 10:
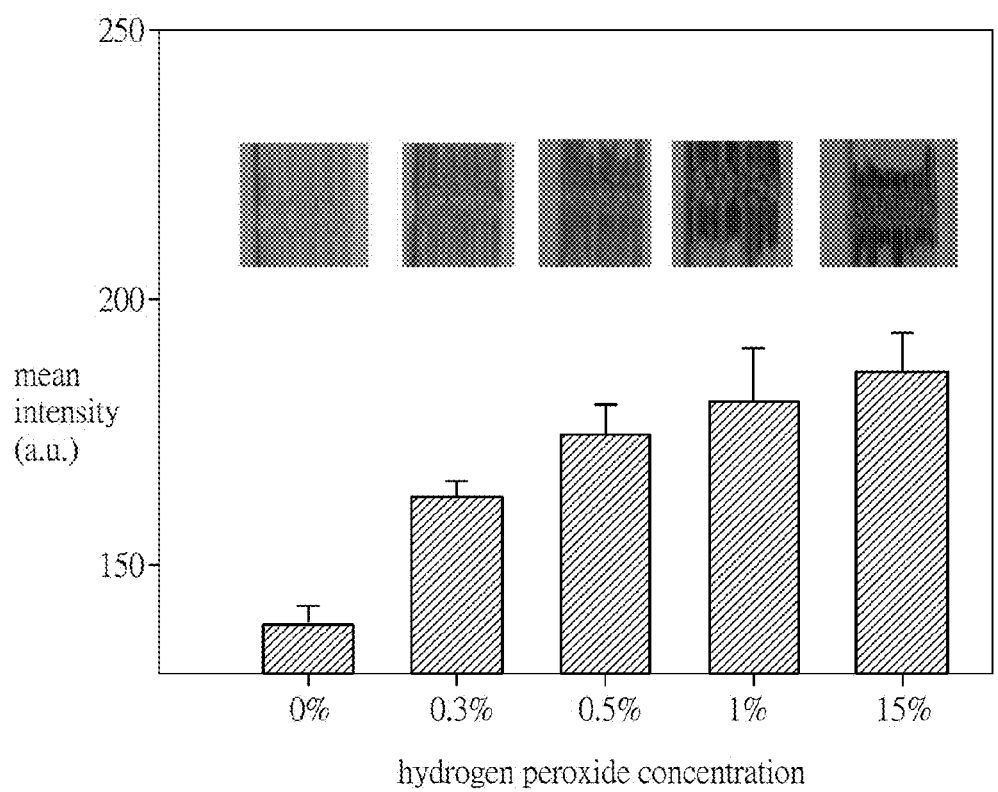
FIG. 10 is a schematic chart showing the detection result as using the detection device of FIG. 1 to detect hydrogen peroxide.

The analysis result is shown in FIG. 10. After the test samples react with the chemical reagent, the test result indicates that the detected mean intensity (which is represented in an arbitration unit, a.u.) of the color reaction increases as the hydrogen peroxide concentration increases. At the same time, the color of the reaction portion becomes darker as the hydrogen peroxide concentration increases.

Experimental Example 4: Detecting Pathogenic Microorganism by the Detection Device 1

4 μL 62.5 mM sodium hydroxide solution is dropped (by micropipette (Gilson, Inc.)) onto the reaction portion 13 of the detection device 1. The detection device 1 is dried for 10 minutes at 25° C. Then, 2 μL resazurin solution (0.4% w/v) is dropped to the sodium hydroxide solution, and the detection device 1 is dried for 10 minutes at 25° C. Afterwards, the sampling portions 11 of the detection devices 1 (4 sets) are dipped into different milk samples, which have placed for 0, 4, 8 and 12 hours, followed by the detection of the sour levels of the 4 sets.

Figure 11A:
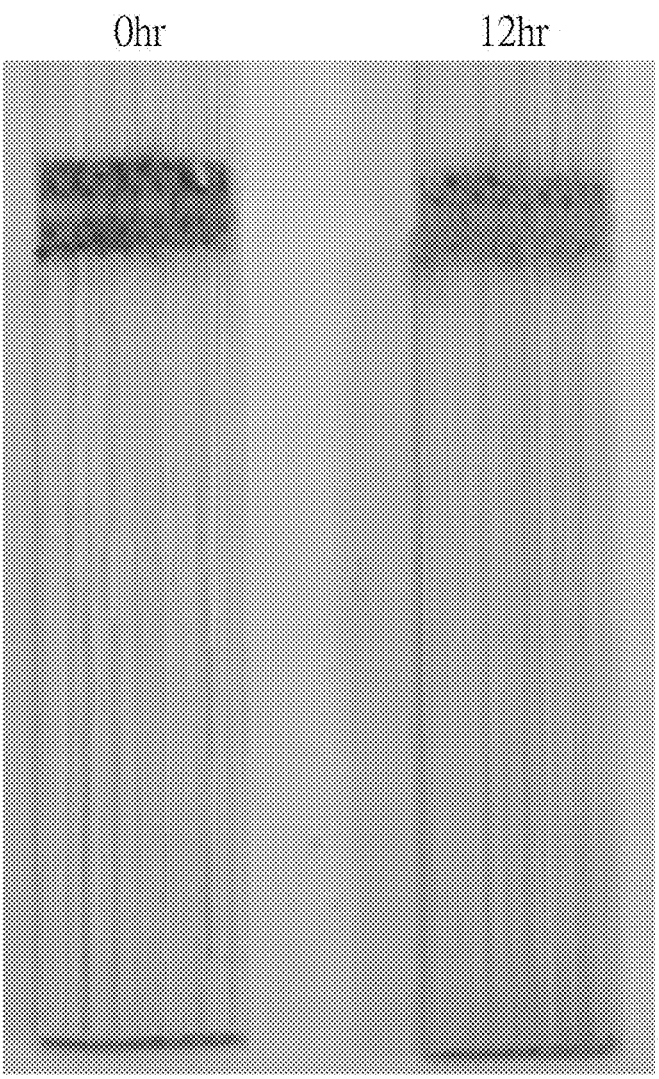
FIGS. 11A and 11B are schematic charts showing the detection results as using the detection device of FIG. 1 to detect pathogenic microorganisms.
Figure 11B:
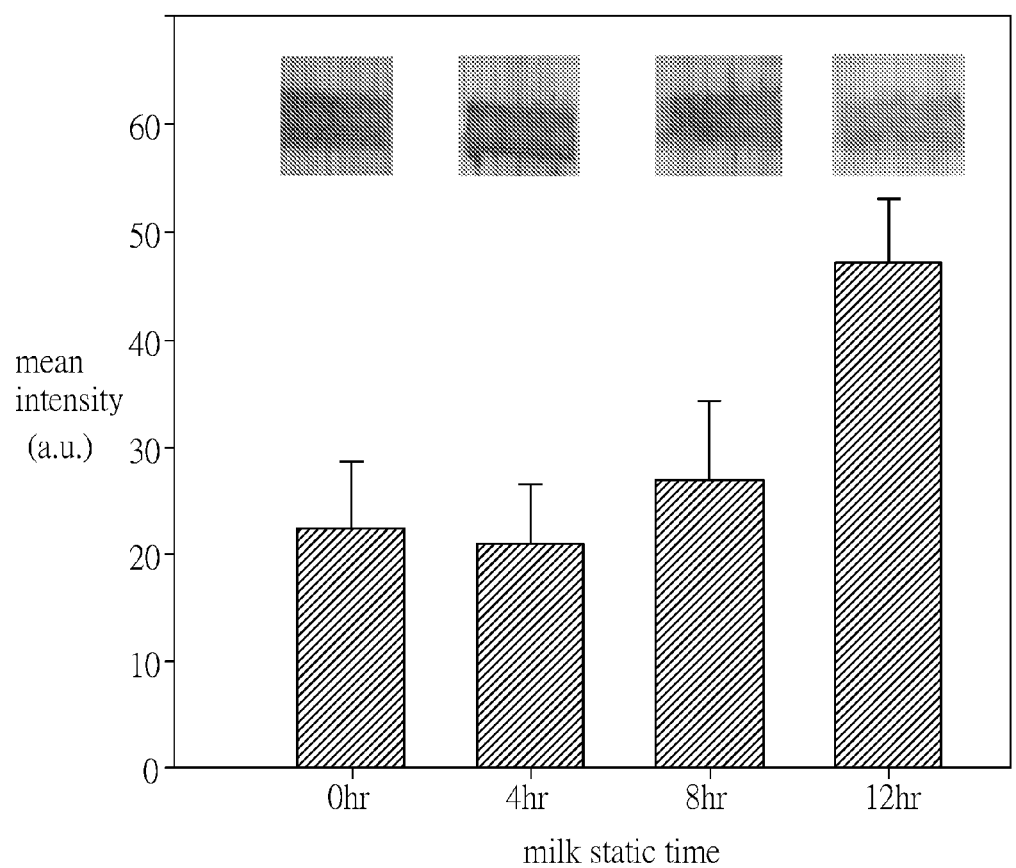

The analysis result is shown in FIGS. 11A and 11B. After the test samples react with the chemical reagent, the test result indicates that the detected mean intensity (which is represented in an arbitration unit, a.u.) of the color reaction changes as the placed time increases. This means that the pathogenic microorganisms grow and increase, which leads to the spoilage of milk, as the placed time of the milk increases. These factors can cause the color reaction of the chemical reagent containing resazurin solution. As shown in the figure, it is proved that the detection device 1 of the embodiment can correctly detect the increased microorganisms as well as the sour level when the placed time increases.

In summary, the food safety detection device of the present invention has a reaction portion containing the chemical reagent for effectively detecting a specific test target such as the concerned nitrite or nitrate in food safety. The food safety detection device includes a main structure composed of xylem fiber substrate, which has excellent absorptive property for water molecules, so that the detection speed can be improved due to the enhanced capillary phenomenon of the liquid test sample in the detection device. In addition, the conventional testing strips, which are made by multiple processes, may contain some residual prohibited or harmful chemical reagents used in the processes, so the food products cannot be served after being detected by the conventional testing strips. In contrary, the food safety detection device of the invention is made of the natural xylem fiber substrate, so it can directly contact or be inserted into a sample and the tested sample can be still served after the detection. Besides, the present invention also has the advantages of lower cost and easy production. Preferably, the xylem fiber substrate has a strengthened mechanical structure and better pH durability than the conventional testing strips (made by papers).

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A food safety detection device comprising:
   a xylem fiber substrate, which is configured with:
   a sampling portion; and
   a reaction portion comprising at least one chemical reagent;
   wherein, the sampling portion absorbs a test sample, the test sample moves on the xylem fiber substrate to the reaction portion and reacts with the chemical reagent, and
   wherein the xylem fiber substrate is further configured with a transmission portion connected to the sampling portion and the reaction portion, and at least a part of the transmission portion is processed by hydrophobic surface treatment,
   the reaction portion has an accommodating space and a bulk body, the accommodating space is formed on a surface of the xylem fiber substrate, at least a part of the bulk body is disposed in the accommodating space, and the chemical reagent is disposed on the bulk body, and the accommodating space is disposed between an opened part and a main part of the xylem fiber substrate,
   the opened part is at least partially connected to the main part, and
   the densification property of the bulk body is greater than that of the reaction portion.

2. The detection device of claim 1, wherein the xylem fiber substrate comprises cellulose, lignin and/or hemicellulose.

3. The detection device of claim 1, wherein the chemical reagent comprises a food additive reagent, a pesticide reagent, or a pathogenic microorganism reagent.

4. The detection device of claim 1, wherein the detection device is a stirring rod, a toothpick or a chopstick.

5. The detection device of claim 2 wherein cellulose is α-cellulose, and the proportion of α-cellulose in the bulk body is greater than that in the reaction portion.

6. A manufacturing method for a food safety detection device, comprising steps of:
   providing a xylem fiber substrate;
   forming a sampling portion and a reaction portion on the xylem fiber substrate;
   disposing at least a chemical reagent in the reaction portion so as to form the detection device, disposing a transmission portion on the xylem fiber substrate, wherein the transmission portion connects to the sampling portion and the reaction portion;

processing at least a part of the transmission portion by hydrophobic surface treatment;

forming an accommodating space and a bulk body in the reaction portion, wherein the accommodating space is disposed between an opened part and a main part of the xylem fiber substrate, and at least a part of the bulk body is disposed in the accommodating space and the opened part is at least partially connected to the main part; and disposing the chemical reagent on the bulk body, wherein the densification property of the bulk body is greater than that of the reaction portion.

7. The manufacturing method of claim 6, wherein the step of providing the xylem fiber substrate comprise providing a raw material containing xylem fiber and to physically process the raw material to extract the xylem fiber substrate.

8. The manufacturing method of claim 6, wherein the xylem fiber substrate comprises cellulose, lignin and/or hemicellulose.

9. The manufacturing method of claim 6, wherein the chemical reagent comprises a food additive reagent, a pesticide reagent, or a pathogenic microorganism reagent.

10. The manufacturing method of claim 6, wherein the detection device is a stirring rod, a toothpick or a chopstick.

11. The manufacturing method of claim 10, further comprising, before the step of providing the xylem fiber substrate, a step of:

shaping the xylem fiber substrate to a shape of stirring rod, a toothpick or a chopstick.

12. The manufacturing method of claim 8, wherein cellulose is $\alpha$-cellulose, and the proportions of $\alpha$-cellulose in the bulk body is greater than that in the reaction portion.

* * * * *